(12) United States Patent
Perel et al.

(10) Patent No.: US 7,078,712 B2
(45) Date of Patent: Jul. 18, 2006

(54) IN-SITU MONITORING ON AN ION IMPLANTER

(75) Inventors: Alexander S. Perel, Danvers, MA (US); Lyudmila Stone, Lynnfield, MA (US); William K. Loizides, Lee, NH (US); Victor M. Benveniste, Gloucester, MA (US)

(73) Assignee: Axcelis Technologies, Inc., Beverly, MA (US)

( * ) Notice: Subject to any disclaimer, the term of this patent is extended or adjusted under 35 U.S.C. 154(b) by 224 days.

(21) Appl. No.: 10/803,439

(22) Filed: Mar. 18, 2004

(65) Prior Publication Data
US 2005/0205807 A1    Sep. 22, 2005

(51) Int. Cl.
*H01J 37/304*    (2006.01)
*G01N 21/00*    (2006.01)
*G01N 21/88*    (2006.01)

(52) U.S. Cl. ............... 250/492.21; 250/492.1; 250/492.2; 250/492.3; 356/237.2

(58) Field of Classification Search ........... 250/492.1, 250/492.21, 492.2, 492.3; 356/237.1–237.5
See application file for complete search history.

(56) References Cited

U.S. PATENT DOCUMENTS

| | | | | |
|---|---|---|---|---|
| 3,749,500 A | * | 7/1973 | Carlson et al. ............ 356/638 |
| 3,925,660 A | * | 12/1975 | Albert ...................... 378/45 |
| 4,136,953 A | * | 1/1979 | Klein et al. ............... 356/339 |
| 4,208,126 A | * | 6/1980 | Cheo et al. ................. 356/51 |
| 4,377,340 A | * | 3/1983 | Green et al. ............. 356/237.3 |
| 4,378,159 A | | 3/1983 | Galbraith |
| 4,632,559 A | * | 12/1986 | Brunsting ................ 356/416 |
| 4,641,967 A | | 2/1987 | Pecen |
| 4,770,531 A | * | 9/1988 | Tanaka et al. ............ 356/500 |
| 4,772,126 A | | 9/1988 | Allemand et al. |
| 4,889,998 A | * | 12/1989 | Hayano et al. ........ 250/559.41 |
| 4,893,932 A | * | 1/1990 | Knollenberg ............ 356/369 |
| 5,028,139 A | * | 7/1991 | Kramer et al. ............ 356/446 |
| 5,043,285 A | * | 8/1991 | Surgi ........................ 436/136 |
| 5,255,089 A | | 10/1993 | Dybas et al. |
| 5,317,380 A | * | 5/1994 | Allemand ................ 356/338 |
| 5,402,681 A | * | 4/1995 | Nakaso et al. ............ 73/602 |
| 5,475,728 A | * | 12/1995 | Smith et al. .............. 378/81 |
| 5,633,698 A | * | 5/1997 | Imai ......................... 355/72 |
| 5,636,023 A | * | 6/1997 | Yanagisawa .............. 356/613 |
| 6,005,913 A | * | 12/1999 | Zombo et al. ............ 378/71 |

(Continued)

Primary Examiner—John R. Lee
Assistant Examiner—Bernard E. Souw
(74) Attorney, Agent, or Firm—Eschweiler & Associates, LLC

(57) ABSTRACT

The present invention is directed to in-situ detection of particles and other such features in an ion implantation system during implantation operations to avoid such additional monitoring tool steps otherwise expended before and/or after implantation, for example. One or more such systems are revealed for detecting scattered light from particles on one or more semiconductor wafers illuminated by a light source (e.g., laser beam). The system comprises an ion implanter having a laser for illumination of a spot on the wafer and a pair of detectors (e.g., PMT or photodiode) rotationally opposite from the ion implantation operations. A wafer transport holds a wafer or wafers for translational scanning under the fixed laser spot. A computer analyzes the intensity of the scattered light detected from the illuminated wafer (workpiece), and may also map the light detected to a unique position. For example, particles or other such contaminates may be identified on wafers during the implantation process before additional time and resources are consumed, and aid in determining the sources of such contaminates. Further, threshold analysis of the quantity or size of such particles, for example, may provide a system interlock for shutdown or feedback control.

54 Claims, 13 Drawing Sheets

U.S. PATENT DOCUMENTS

| | | | | |
|---|---|---|---|---|
| 6,062,084 A | * | 5/2000 | Chang et al. | 73/601 |
| 6,078,386 A | * | 6/2000 | Tsai et al. | 356/237.1 |
| 6,081,325 A | * | 6/2000 | Leslie et al. | 356/237.2 |
| 6,239,425 B1 | * | 5/2001 | Hunt | 250/226 |
| 6,271,916 B1 | * | 8/2001 | Marxer et al. | 356/237.3 |
| 6,307,625 B1 | * | 10/2001 | Sharts et al. | 356/301 |
| 6,331,704 B1 | * | 12/2001 | Owen | 250/339.11 |
| 6,485,413 B1 | * | 11/2002 | Boppart et al. | 600/160 |
| 6,587,575 B1 | * | 7/2003 | Windham et al. | 382/110 |
| 6,597,006 B1 | * | 7/2003 | McCord et al. | 250/559.19 |
| 6,606,153 B1 | * | 8/2003 | Marxer et al. | 356/237.3 |
| 6,627,889 B1 | * | 9/2003 | Ochiai et al. | 250/310 |
| 6,741,347 B1 | * | 5/2004 | Scaiano et al. | 356/319 |
| 6,778,267 B1 | * | 8/2004 | Drake | 356/237.1 |
| 6,782,337 B1 | * | 8/2004 | Wack et al. | 702/155 |
| 6,806,951 B1 | * | 10/2004 | Wack et al. | 356/237.2 |
| 6,843,927 B1 | * | 1/2005 | Naser-Ghodsi | 216/84 |
| 6,888,627 B1 | * | 5/2005 | Leslie et al. | 356/237.2 |
| 6,891,627 B1 | * | 5/2005 | Levy et al. | 356/625 |
| 6,917,419 B1 | * | 7/2005 | Fielden et al. | 356/237.2 |
| 6,919,957 B1 | * | 7/2005 | Nikoonahad et al. | 356/237.2 |
| 6,922,236 B1 | * | 7/2005 | Vaez-Iravani et al. | 356/237.2 |
| 6,946,394 B1 | * | 9/2005 | Fielden et al. | 438/680 |
| 6,950,196 B1 | * | 9/2005 | Fielden et al. | 356/630 |
| 2002/0051130 A1 | * | 5/2002 | Marxer et al. | 356/237.3 |
| 2002/0131166 A1 | * | 9/2002 | Woo et al. | 359/391 |
| 2003/0206294 A1 | * | 11/2003 | Leslie et al. | 356/237.2 |
| 2003/0227619 A1 | * | 12/2003 | Leslie et al. | 356/237.2 |
| 2004/0080741 A1 | * | 4/2004 | Marxer et al. | 356/237.3 |
| 2004/0244694 A1 | * | 12/2004 | Hayashi | 118/728 |
| 2005/0018182 A1 | * | 1/2005 | Hyun et al. | 356/237.4 |
| 2005/0046848 A1 | * | 3/2005 | Cromwell et al. | 356/417 |
| 2005/0111727 A1 | * | 5/2005 | Emery | 382/145 |
| 2005/0139789 A1 | * | 6/2005 | Nagano et al. | 250/492.23 |
| 2005/0205807 A1 | * | 9/2005 | Perel et al. | 250/492.21 |
| 2005/0206804 A1 | * | 9/2005 | Hara | 349/62 |
| 2005/0266448 A1 | * | 12/2005 | Hagiwara et al. | 435/6 |

* cited by examiner

IN-SITU MONITORING ON AN ION IMPLANTER

FIELD OF THE INVENTION

The present invention relates generally to ion implantation systems, and more particularly to monitoring contaminate particles, features and feature damage, temperatures and other such detectable quantities in such systems during ion implantation.

BACKGROUND OF THE INVENTION

Ion implantation systems are used to impart impurities, known as dopant elements, into semiconductor substrates or wafers, commonly referred to as workpieces. In such systems, an ion source ionizes a desired dopant element, and the ionized impurity is extracted from the ion source as a beam of ions. The ion beam is directed (e.g., swept) across respective workpieces to implant ionized dopants within the workpieces. The dopant ions alter the composition of the workpieces causing them to possess desired electrical characteristics, such as may be useful for fashioning particular semiconductor devices, such as transistors, upon the substrates.

The continuing trend toward smaller electronic devices has presented an incentive to "pack" a greater number of smaller, more powerful and more energy efficient semiconductor devices onto individual wafers. Moreover, semiconductor devices are being fabrication upon larger workpieces to increase product yield. For example, wafers having a diameter of 300 mm or more are being utilized so that more devices can be produced on a single wafer. This necessitates careful monitoring and control over semiconductor fabrication processes, including ion implantation.

However, operation of an ion implanter or other ion beam equipment (e.g., linear accelerators) may result in the production of contaminant particles that in some cases may adhere to the wafers. The contaminant particles, for example, may be less than 1 μm in size. Particles that adhere to wafers during implant are often measured by putting wafers in a particle detection tool employed before and after ion implantation. Detection tool operations take additional capitol investment, consume additional time and resources, and present a potential exposure to further wafer contamination.

Such wafers are expensive and, thus, make it very desirable to mitigate waste, such as having to scrap an entire wafer due to particle contamination detected after ion implantation, after time and resources have already been invested. Further, detection after ion implantation makes it difficult to trace the source and causes of particles and other contaminates in such processes requiring numerous steps. In addition, it is desirable to minimize the use of traditional detection tools that may also provide a source of contamination and consume more time and resources.

SUMMARY OF THE INVENTION

The following presents a simplified summary in order to provide a basic understanding of one or more aspects of the invention. This summary is not an extensive overview of the invention, and is neither intended to identify key or critical elements of the invention, nor to delineate the scope thereof. Rather, the primary purpose of the summary is to present some concepts of the invention in a simplified form as a prelude to the more detailed description that is presented later.

The present invention is directed to in-situ monitoring of particles and other such features in a single wafer or batch ion implantation system during implantation to avoid such additional detection tool steps otherwise expended before and after implantation, for example. Multiple arrangements are provided for detecting the light scattered from a light source such as a laser light source. For example, using laser light scattering in the end station of a single wafer or spinning disc batch ion implantation system, particles can be detected on the wafer(s) (workpiece(s)) surface during an ion implant. The disk rotation and/or a linear scan may be used to scan all points on all wafers. In this manner, the implantation process can be monitored so that the wafer is implanted with a more uniform concentration of ions, having minimal particle contamination and detection operations.

According to one or more aspects of the present invention, the system comprises a batch ion implanter having a laser for illumination of a spot on the wafer and one or more (e.g., a pair of) detectors (e.g., PMT or photodiode) rotationally opposite from the ion implantation operations. In one implementation of the present invention, a spinning disk transport in the end station holds the batch of wafers for rotational scanning of the wafers (x axis) under the fixed laser spot, while a linear transport scans the wafers over their full height (y axis). In the present invention, both the ion implanter and the in-situ detection system use the same rotational and linear scanning motions.

The present invention further includes a computer or another such processor that analyzes the intensity of the scattered light detected from the illuminated wafer. The computer maps the detected light to a unique position determined by encoder counts associated with the rotary and linear transport positions of the wafer scans. In another aspect of the invention, the processor analyzes the light mapped to the unique positions on the workpieces to determine patterns of light corresponding to, for example, particles, scratches, features, feature damage, or the temperature of the wafers. In another aspect of the invention, the magnitude of the scattered light may be employed to detect the existence of particles as well as estimate the sizes thereof in a binning procedure, wherein the magnitude of scattered light correlates to a scattered light magnitude of baseline particle. Such binning may further be employed to ascertain a source of the particles, as may be desired.

In a further aspect of the present invention, threshold analysis of the quantity or size of such particles, for example, may provide a system interlock for shutdown or feedback control for the ion implantation. In this way, for example, particles or other such contaminates may be identified on wafers during the implantation process before additional time and resources are consumed, to aid in determining the sources of such contaminates.

An end station or process chamber downstream of the laser and ion beams is also included to hold the one or more workpieces toward which the laser and ion beams are directed. Finally, the detector of the in-situ monitoring system includes one or more lens, filters, and a slit aligned with the linear motion to pass the scattered light imaged to the detector and to mask specular reflected light from the light source (e.g, laser light) from saturating the detector. One implementation of the present invention, provides a pair of such detectors mounted on opposing sides of the laser source to maximize the measured signal from the scattered light, to present improved detection perspective, and for increased detection resolution.

According to another aspect of the invention, a one-dimensional or two-dimensional scan, single workpiece system is disclosed having an in-situ particle detection and/or monitoring system associated therewith. The system comprises a transport for providing a scan transport to the workpiece and an in-situ monitoring system. The monitoring system comprises a light source configured to provide a beam of illumination to at least a portion of a workpiece, and a detector adapted to capture scattered light from the illuminated portion of the workpiece. Based on the scattered light, conclusions can be drawn regarding the existence of particles in the system.

In accordance with one or more other aspects of the present invention, an in-situ monitoring system suitable for use in detecting contaminate particles on one or more workpieces in a spinning disc batch ion implanter is disclosed. The system includes an ion implanter for producing a beam of ions and directing the beam of ions downstream toward the workpieces held within an end station, and an in-situ monitoring system suitable for detecting particles or features on the one or more workpieces during ion implantation. The monitoring system also includes the one or more workpieces held in the end station, a rotary scan transport for providing rotary motion to the workpieces including an encoder count of the radial scan position, and a linear scan transport for providing reciprocating linear motion to the workpieces including an encoder count of the linear scan position. The monitoring system further includes a light source for providing a fixed beam of illumination to a portion of one of the workpieces, and a detector for capturing scattered light from the illuminated portion of the workpiece. Finally, the monitoring system includes a processor for analyzing the intensity of the scattered light detected from the illuminated workpiece, and for mapping the light detected to a unique position determined by the encoder counts associated with the rotary and linear transport positions of the workpiece scan.

To the accomplishment of the foregoing and related ends, the following description and annexed drawings set forth in detail certain illustrative aspects and implementations of the invention. These are indicative of but a few of the various ways in which the principles of the invention may be employed. Other aspects, advantages and novel features of the invention will become apparent from the following detailed description of the invention when considered in conjunction with the drawings.

DETAILED DESCRIPTION OF THE INVENTION

Figure 1:
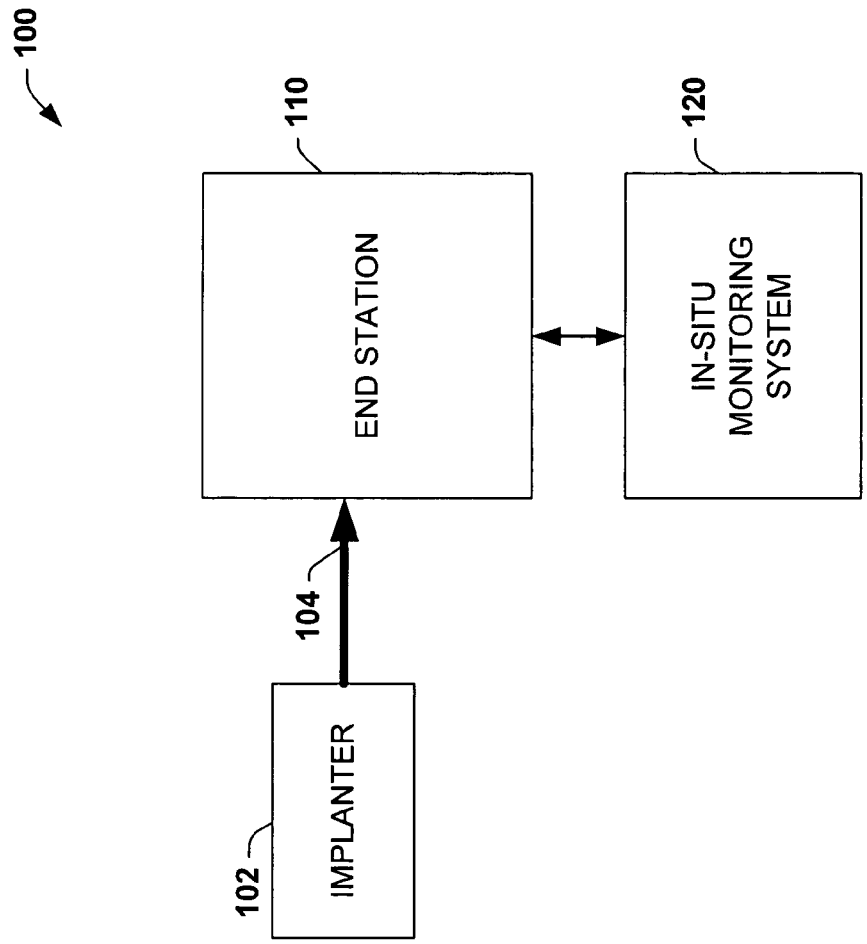
FIG. 1 is a block diagram illustrating components of an ion implantation system having an in-situ monitoring system according to one or more aspects of the present invention to detect particles on one or more workpieces during ion implantation.

The present invention will now be described with reference to the drawings wherein like reference numerals are used to refer to like elements throughout. The illustrations and following descriptions are exemplary in nature, and not limiting. Thus, it will be appreciated that variants of the illustrated systems and methods and other such implementations apart from those illustrated herein are deemed as falling within the scope of the present invention and the appended claims.

The present invention relates to detecting scattered light (e.g., from a light source such as a laser) produced by particles or other such detectable features and quantities on one or more workpieces during ion implantation in an ion implantation system to determine the source and causes of the particles in ion implantation, for example. Multiple arrangements are revealed for detecting light scattered from the workpieces (e.g., wafers) illuminated by a light source such as a laser light source. For example, the intensity or number of photons detected from the scattered light is mapped against the X-Y position of a laser illuminated spot on each wafer. A processor such as a computer, for example, then analyzes patterns of the detected scattered light corresponding to particles, features, or even the thermal profile of the workpieces. By spinning and cyclically shuttling or otherwise moving the wafers under a fixed laser light beam, all portions of each wafer may be illuminated and thoroughly monitored at one location on the process chamber or end station, while ions are implanted at another. Thus, monitoring time may be advantageously saved, with no additional handling costs or inherent contamination risks.

The analyzed pattern information and/or particle detections, may further be used to interlock the system or otherwise provide feedback to shutdown the ion implantation operation if a critical threshold level of particles is detected on the wafers. This operational aspect of the present invention may mitigate additional time and resources from otherwise being consumed and wasted.

In one aspect of the present invention, the system may be employed in the context of a particle troubleshooting procedure, wherein one or more structural or implant process variables are varied and particle generation is monitored in conjunction therewith. In such a context, one can determine whether certain physical or process variables are a cause of particle generation. Further, in conjunction with the binning procedure to ascertain particle contamination size, various particle generation modes or causes may be investigated and/or confirmed.

Referring initially to FIG. 1, an ion implantation and monitoring system 100 suitable for implementing one or more aspects of the present invention is depicted in block diagram form. The system 100 includes an ion implanter 102 for producing a quantity of ions that can be extracted in the form of an ion beam 104. The ion implanter 102 generally includes an ion source having a gas source from which the ions are generated, and a power source that facilitates the production of the ions from the gas.

The ion implantation system 100 further includes an end station 110 to receive the ion beam 104 directed through a beamline assembly (not shown). The end station 110 supports one or more workpieces such as semiconductor wafers (not shown) for implantation by the ion beam 104. The end station 110 includes a target scanning system (not shown) for translating or scanning one or more target workpieces and the ion beam 104 relative to one another. The target scanning system may provide for batch or serial implantation, for example, as may be desired under given circumstances, operating parameters and/or objectives. Although the term end station is used in the present example, it should be understood that the term end station is to be construed broadly to include any type of implantation process chamber, as may be appreciated. All such process chambers are contemplated as falling within the scope of the present invention.

Additionally, an in-situ monitoring system 120 is operatively coupled to the end station 110 to detect, for example, particles, features, or the temperatures of the one or more workpieces during ion implantation in accordance with the present invention. The monitoring system 120 may include, for example, a photomultiplier (PMT) or photodiode (not shown) that is operable to detect the intensity of scattered light from an illuminated spot on one or more of the wafers as the wafers are scanned past a fixed beam of the illumination (not shown). In accordance with one or more aspects of the present invention, the detected scattered light may be displayed for operator particle determination and/or the detected light may be analyzed (e.g., via a processor—not shown) to determine patterns of the light corresponding to particles. Although system 120 is operable to monitor or detect particles, for example, during ion implantation, it will be appreciated that monitoring may therefore, also be accomplished before, during, or after ion implantation in accordance with the present invention. In addition, for a batch system, although a single blank test wafer is employed for analysis of particles, alternately all the production wafers may be evaluated for particles, taking into account additional scattering that may be a function of features fabricated thereon.

Figure 2:
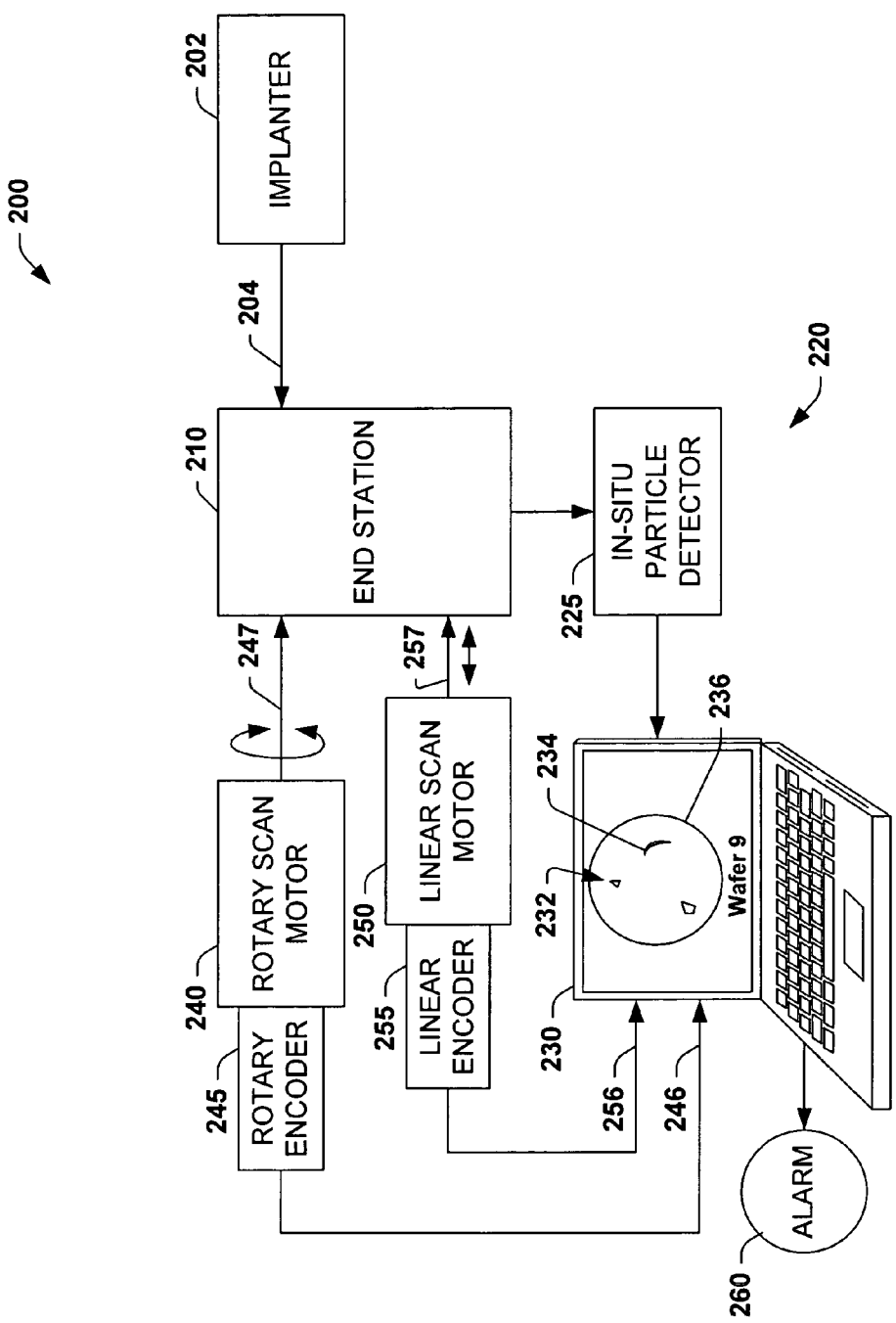
FIG. 2 is a more detailed block diagram illustrating components of an ion implantation system having an in-situ monitoring system according to one or more aspects of the present invention to detect particles on one or more workpieces during ion implantation.

FIG. 2, illustrates in block diagram form further details of an ion implantation and monitoring system 200 suitable for implementing one or more aspects of the present invention. The system 200 includes an ion implanter 202 for producing a quantity of ions that can be extracted in the form of an ion beam 204. The ion implanter 202 may include an ion source and a gas source from which the ions are generated, and a power source that facilitates the production of the ions from the gas.

The ion implantation system 200 further includes an end station 210 to receive the ion beam 204 directed through a beamline assembly (not shown). The end station 210 supports one or more workpieces such as semiconductor wafers (not shown) for implantation by the ion beam 204. The end station 210 includes a target scanning system (not shown) for translating or scanning one or more target workpieces and the ion beam 204 relative to one another. The target scanning system may provide for batch or serial implantation, for example, as may be desired under given circumstances, operating parameters and/or objectives.

Additionally, an in-situ monitoring system 220 is operatively coupled to the end station 210 to detect, for example, particles, features, or the temperatures of the one or more workpieces during ion implantation in accordance with the present invention. The monitoring system 220 may include, for example, an in-situ particle detector 225 comprising a photomultiplier (PMT) or photodiode (not shown) that is operable to detect the intensity of scattered light from an illuminated spot on one or more of the wafers as the wafers are scanned past a fixed beam of the illumination (not shown).

In accordance with one or more aspects of the present invention, the detected scattered light may be mapped against X-Y scanning motion data and displayed for operator particle determination and/or the detected light may be analyzed by a processor or computer 230 to determine patterns of the light corresponding to particles 232 or other features 234 on a wafer 236. Although system 220 is operable to monitor or detect particles 234, for example, during ion implantation, it will be appreciated that monitoring may therefore, be accomplished before, during, or after ion implantation in accordance with the present invention.

In accordance with a further aspect of the present invention, the X-Y scanning motion data is obtained from rotary and linear scan encoder counts. A rotary drive (scan) motor 240 provides rotational drive to the disk (not shown) in the end station 210 of, for example, a spinning disk ion implanter. A rotary encoder 245 attached to the rotary drive motor 240 provides rotary encoder counts 246 representing the wafer X motion 247, for example. A linear drive (scan) motor 250 provides linear transport of the disk (not shown) in the end station 210 of, for example, a spinning disk ion implanter. A linear encoder 255 attached to the linear drive motor 250 provides linear encoder counts 256 representing the wafer Y motion 257, for example. Alternately, the encoders 245, 255 may provide r (magnitude) and θ (angle) coordinates in a polar coordinate or other format, as may be desired.

The processor or computer 230 of the present invention maps the scattered light detected against rotary encoder counts 246 and the linear encoder counts 256 representing the wafer X-Y motion, 247 and 257 respectively. The computer 230 then displays the map of the detected light and the motion data as pixels of image data associated with the wafer 236. In accordance with another aspect of the present invention, the computer analyzes the wafer image data to identify and/or count patterns of the light corresponding to particles 232, features 234, or a thermal map of the wafer. In another aspect of the invention, the analysis that determines the count of particles, for example, may be used to trigger an alarm 260 or another such system interlock operable to shutdown the system if an acceptable particle count is exceeded in any wafer or region of a wafer, for example.

In addition, the processor 230 may be operable to bin the detected particles in a plurality of binning categories based on the magnitude of the detected scattered radiation. For example, by performing a baseline scattering procedure, a number of known particles, for example, polystyrene spheres of a known size, may be scanned to identify a range in which scattered light is detected for such particles. Then, when particles are detected in the present system, the magnitude of the scattered light can be identified and a conclusion can be made that by falling within a predetermined range, the detected particle correlates to a known particle within that range. That is, one can conclude that although not exactly the same size, the particle provided an equivalent scattering profile, and an estimation of its size can be made therefrom.

Figure 3:
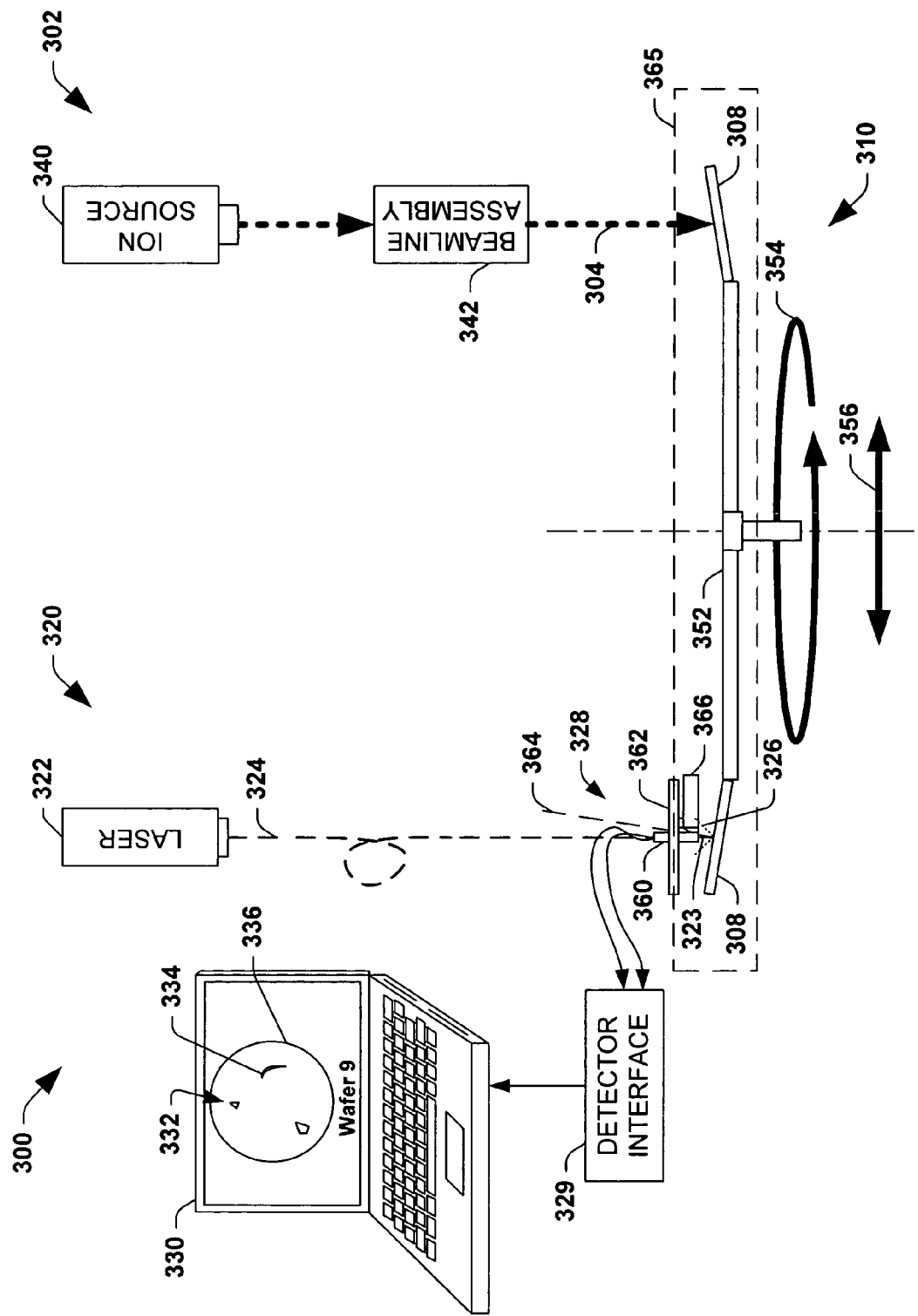
FIG. 3 is a cross sectional side view illustrating functional aspects and components of an ion implantation system having an in-situ monitoring system according to one or more aspects of the present invention to detect particles on one or more workpieces during ion implantation.

FIG. 3 illustrates functional aspects and components of an ion implantation system 300 having an in-situ monitoring system used in accordance with the present invention and the systems of FIGS. 1 and 2 used to detect particles on one or more workpieces during ion implantation. The ion implantation and monitoring system 300 comprises an ion implanter 302 directing an ion beam 304 toward one or more workpieces 308 held in an end station 310, and an in-situ monitoring system 320. The system 320 includes a light source 322 (e.g., laser) that directs a laser beam 323, for example, via an optical fiber 324 toward the one or more workpieces 308 held in the end station 310.

The laser beam 323 of the in-situ monitoring system 320 illuminates a spot on one of the workpieces 308 to produce scattered light 326 received by a detector assembly 328. The signal of the detected scattered light 326 may be further conditioned by a detector interface 329 for display and analysis by a computer processor 330. As described in association with FIGS. 1 and 2, the processor 330 maps the detected scattered light against X-Y scanning motion data and displays the detected light patterns. The operator and/or the processor 330 then makes an analysis of the light patterns to identify patterns of the light corresponding to particles 332 or other features 334 on a wafer 336. The in-situ monitoring system 320 is operable to detect, for example, particles, features, or temperatures on the one or more workpieces 308 during ion implantation in accordance with the present invention. Although system 320 is operable to monitor or detect particles 334, for example, during ion implantation, it will be appreciated that monitoring may therefore, be accomplished before, during, or after ion implantation in accordance with the present invention.

The ion implanter 302 of system 300 further includes an ion source 340 for producing a quantity of ions extracted in the form of an ion beam 304 directed through a beamline assembly 342 toward the end station 310. The end station 310 supports the one or more workpieces 308 such as semiconductor wafers for implantation by the ion beam 304. The end station 310 includes a target scanning system for scanning or translating one or more target workpieces 308 and the ion beam 304 relative to one another. For example, an embodiment of the present invention uses a spinning disk wafer support 352 to produce a rotary scanning motion 354 to scan all the wafers past the fixed ion beam 304 and also past the fixed laser beam 323. This rotary motion provides a circular line scan of the ion beam and the laser beam through all the wafers. To cover the whole wafer, a linear motion 356 is provided to the one or more target workpieces 308 in the end station. The target scanning system may provide for batch or serial implantation, for example, as may be desired under given circumstances, operating parameters and/or objectives.

The in-situ monitoring system 320 of the present invention may include an in-situ particle detector 328 having one or more detectors 360 comprising, for example, a photomultiplier (PMT) or photodiode. Held by flange 362, detector 360 is operable to detect the intensity of scattered light 326 from an illuminated spot on one or more of the wafers 308 scanned past a fixed beam (e.g., laser) of the illumination. In an exemplary implementation of the present invention, the wafers 308 are held at a non-zero angle relative to the plane of rotation of the wafer support 352 and non-perpendicular to the laser beam 323. The non-zero wafer angle (non-perpendicular angle between the wafer 308 and the laser beam 323) requires a slit in the detectors 360 to serve both as a mask for specular laser reflections 364 and as a window to pass the scattered light 326 to the detector 360.

According to another alternative aspect of the invention, the system may include a wafer oriented at approximately a zero angle with respect to the plane of rotation of the wafer support 352. In such an instance, a generally circular aperture may be employed within the detectors 360 for detection of the scattered light, as may be desired. Such alternative arrangements are contemplated as falling within the scope of the present invention.

Below the detector flange 362, a portion of the detector assembly 328 and the entire spinning disk wafer support 352 including the wafers 308 are enclosed within an evacuated process chamber 365. The detector assembly 328 also includes a laser beam trap or beam dump 366 to attenuate the specular laser reflections 364 which may otherwise overwhelm the detector due to reflections within the evacuated chamber 365.

Figure 4:
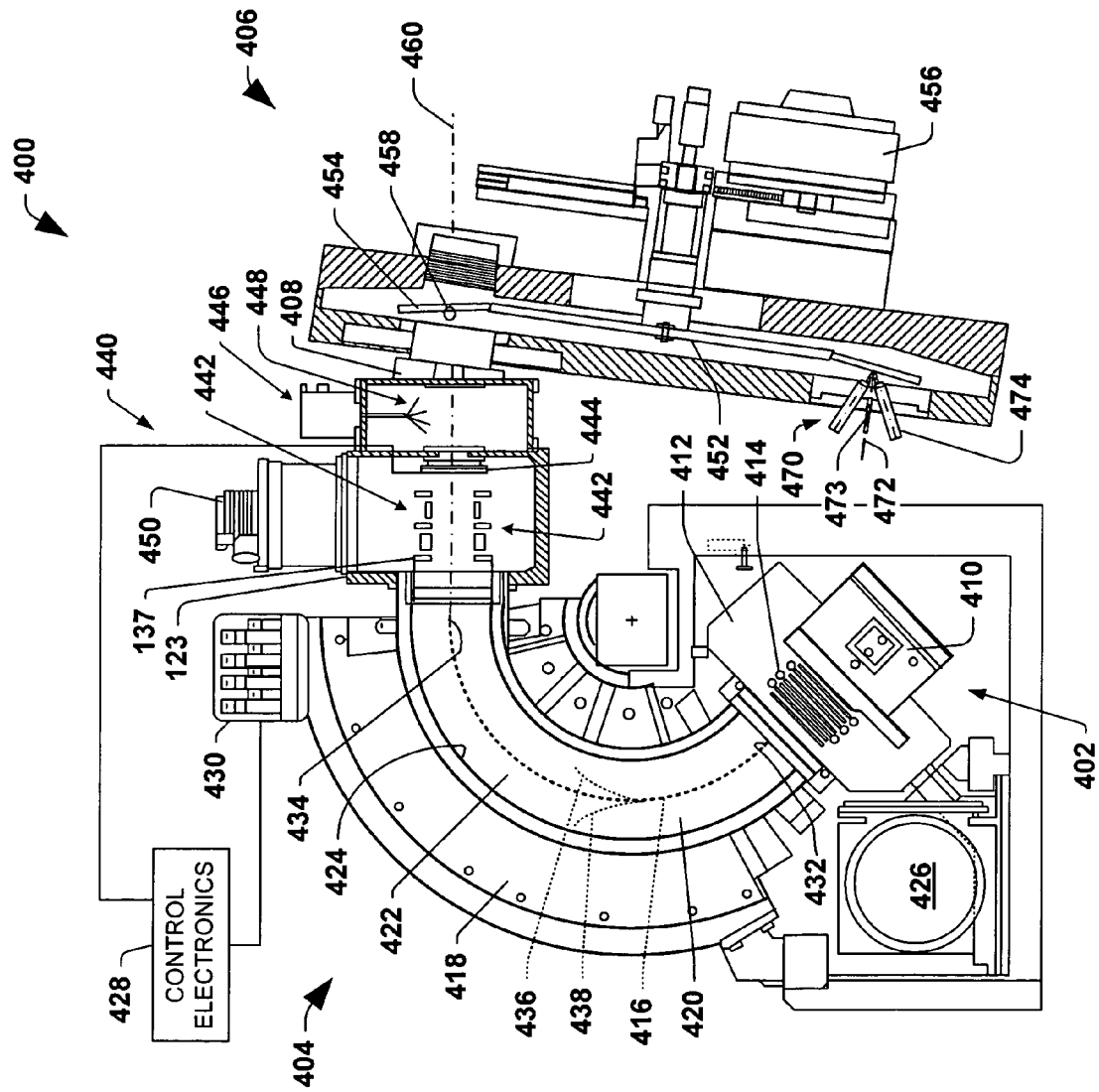
FIG. 4 is a cross sectional side view illustrating an exemplary ion implantation and in-situ monitoring system in accordance with one or more aspects of the present invention.
Figure 5:
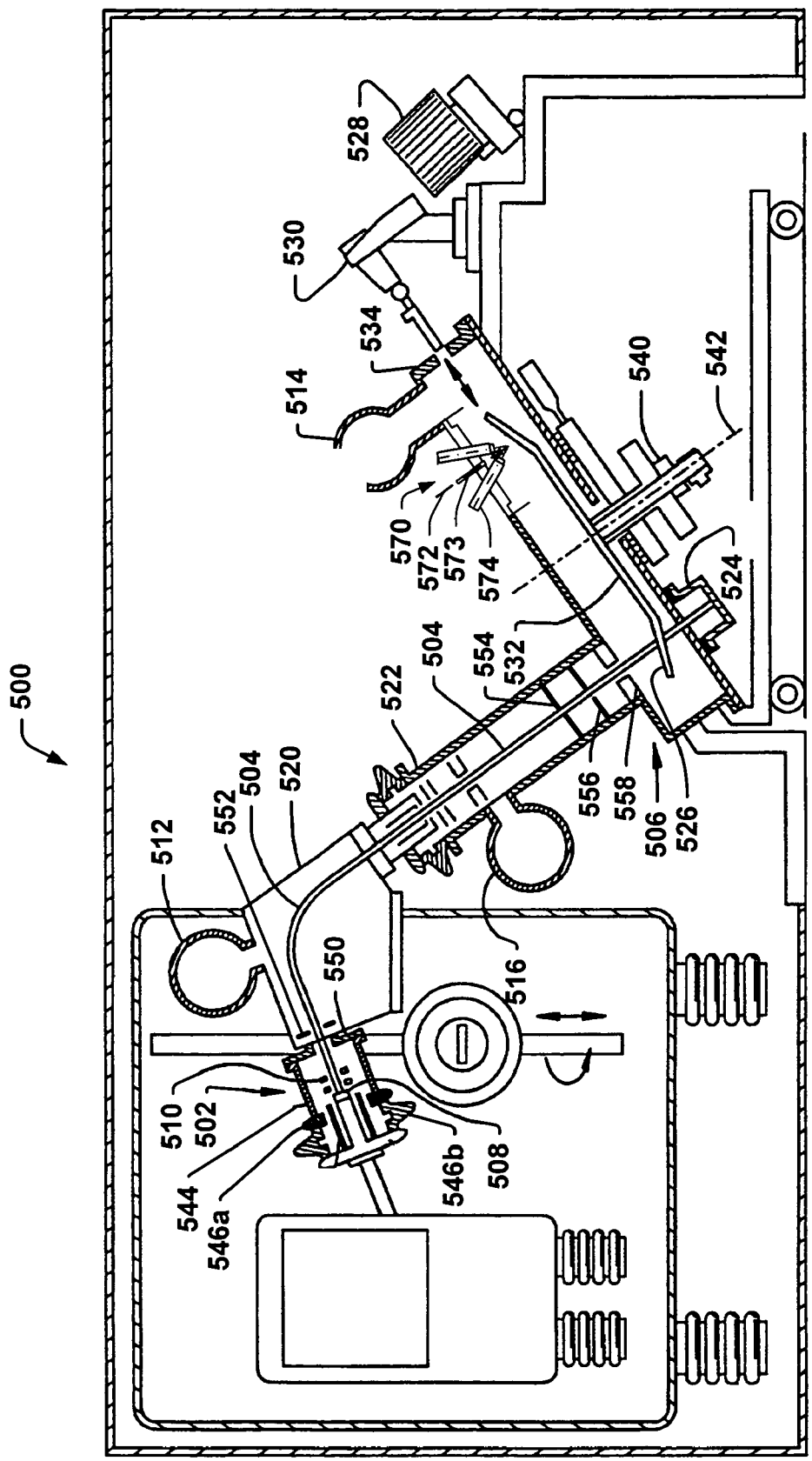
FIG. 5 is a cross sectional side view of another exemplary ion implantation and in-situ monitoring system in accordance with one or more aspects of the present invention.

FIGS. 4 and 5 are presented to illustrate exemplary ion implantation systems 400 and 500, respectively, suitable for implementing one or more aspects of the present invention of FIGS. 1–3 for in-situ monitoring or detecting particles and other such features, and temperatures on the workpieces during implantation. As such, some details of these ion implantation systems will be generally described to illustrate the basic context of exemplary systems for the in-situ monitoring of the present invention.

Referring now to FIG. 4, an exemplary ion implantation system 400 suitable for implementing one or more aspects of the present invention is depicted in somewhat greater detail. Note that although the system in FIG. 4 illustrates a low energy system, it should be appreciated that the system 400 is provided as an example, and that the present invention finds utility in various types of ion implantation systems, and such variations are contemplated as falling within the scope of the present invention. The system 400 includes an ion source 402, a beamline assembly 404, and a target or end station 406. An expansible stainless steel bellows assembly 408, which permits movement of the end station 406 with respect to the beamline assembly 404, connects the end station 406 and the beamline assembly 404.

The ion source 402 comprises a plasma chamber 410 and an ion extraction assembly 412. Energy is imparted to an ionizable dopant gas to generate ions within the plasma chamber 410. Generally, positive ions are generated, however, the present invention is also applicable to systems wherein negative ions are generated by the source 402. The positive ions are extracted through a slit in the plasma chamber 410 by the ion extraction assembly 412, which comprises a plurality of electrodes 414. Accordingly, the ion extraction assembly 412 functions to extract a beam 216 of positive ions from the plasma chamber 410 and to accelerate the extracted ions into the beamline assembly 404, and more particularly into a mass analysis magnet 418 within the beamline assembly 404.

The mass analysis magnet 418 includes a curved beam path 420 within a passageway 422 defined by a metal (e.g., aluminum) beam guide having side-walls 424, evacuation of which is provided by a vacuum pump 426. The ion beam 416 that propagates along this path 420 is affected by the magnetic field generated by the mass analysis magnet 418, to reject ions of an inappropriate charge-to-mass ratio. Control electronics 428 are included to adjust the strength and orientation of this dipole magnetic field, among other things. The magnetic field is controlled by the electrical current through the field windings of the magnet 418 through a magnet connector 430. The control electronics 428 may include a processor and/or computer system for overall control of the system 400.

The dipole magnetic field causes the ion beam 416 to move along the curved beam path 420 from a first or entrance trajectory 432 near the ion source 402 to a second or exit trajectory 434 near an exiting end of the passageway 422. Portions 436 and 438 of the beam 416, comprised of ions having an inappropriate charge-to-mass ratio, are deflected away from the curved trajectory and into the beam guide side walls 424. In this manner, the magnet 418 only allows those ions in the beam 420 which have the desired charge-to-mass ratio to traverse entirely through the passageway 422.

The beamline assembly 404 can also be said to include an accelerator 440. The accelerator 440 includes a plurality of electrodes 442 arranged and biased to accelerate and/or decelerate ions, as well as to focus, bend and decontaminate the ion beam. A dosimetry indicator such as a Faraday cup 444 may also be included to detect a sample current of the ion beam. A source of plasma 446 may also be included to provide a plasma shower 448 for neutralizing a (positive) charge that would otherwise accumulate on a target workpiece as a result of being implanted by the (positively) charged ion beam 416. A vacuum pump 450 may further be included to evacuate the accelerator 440.

Downstream of the accelerator 440 is the end station 406, which includes a wafer support or disk 452 upon which one or more wafers 454 or other such workpieces to be treated are mounted. The wafer support 452 resides in a target plane that is generally oriented relatively perpendicularly to the direction of the implant beam, although the wafer support may also be oriented at angles substantially different from that shown and described. Wafer support may also, for example, take the form of a mechanical arm capable of moving a wafer through the beam or a rotating disk. FIG. 4 illustrates a disc shaped wafer support 452 that is rotated by a motor 456 at the end station 406. The ion beam thus strikes wafers mounted to the support as they move in a circular path. The end station 406 pivots about point 458, which is the intersection of the path 460 of the ion beam and the wafer 454, so that the target plane is adjustable about this point 458.

The ion implantation system 400 further includes a monitoring system having a detector assembly 470 to detect particles, features, and other such detectable quantities on the one or more wafers 454 or other workpieces, for example, before, during, or after ion implantation. The monitoring system 470 may be mounted rotationally opposite from the ion beam path 460 on the process chamber, for example, or at another angular position. The monitoring system 470 includes a light source 472, for example, a laser light source directed by an optical fiber 473 toward the one or more wafers 454 or other workpieces mounted on the spinning support disk 452.

In accordance with the present invention, the detector assembly 470 also includes one or more detectors 474 to receive scattered light from a spot on the wafers 254 illuminated by the laser light 472. The wafers 454 mounted on the wafer support 452 rotates and traverses under the beam of laser light 472 during ion implantation to detect the scattered light from the full surface of the wafers 454. In another aspect of the invention, the detected light may then be mapped with respect to X-Y motion encoder positions corresponding to each wafer (e.g., using a processor or computer) for image display and/or particle or other such feature analysis.

Referring now to FIG. 5, an ion implantation system 500 is illustrated wherein ion beam current may be modulated in accordance with one or more aspects of the present invention. The system includes an ion beam source assembly 502 that produces ions and accelerates the ions along a path to form an ion beam 504. Ions in the beam 504 traverse a path from the ion beam source assembly 502 to impinge on a workpiece or wafer 526 (e.g., silicon wafers) at an implantation station 506. At one typical implantation station, the ion beam 504 impacts silicon wafers 526 to selectively introduce ion particles that dope the wafers 526.

In the example illustrated, the ion beam 504 traverses a generally fixed path of travel. Control over ion implantation dose is maintained, in part, by selective movement of the silicon wafers 526 through the ion beam 504. The ion beam source assembly 502 can utilize a microwave generator and/or a filament, for example, to excite free electrons in the interior of an ion generation or arc chamber 508. The electrons collide with gas molecules injected into the arc chamber interior and ions are thereby generated. The generated ions are accelerated from the arc chamber 508 and formed into an ion beam 504 by an extraction suppression electrode 510. Ions entering the implantation chamber 506 may have an initial energy of up to about 90 KeV, for example, due in part to the effects of the extraction suppression electrode 510.

The ion beam 504 travels through an evacuated path to the implantation station 506. The evacuated path is provided by vacuum pumps 512, 514. The ions that make up the ion beam 504 enter an analyzing magnet 520 that bends the charged ions toward the implantation station 506. Ions having multiple charges and different species ions having the wrong atomic number are lost from the beam 504 due to ion interaction with the magnetic field set up by the analyzing magnet 520. Ions traversing the region between the analyzing magnet 520 and the implantation station 506 are accelerated to even higher energy by an accelerating electrode 522 before impacting wafers 526 at the implantation station 506. A source of plasma 516 is included to bathe the beam 504 in neutralizing plasma that mitigates the number of positive charges that would otherwise accumulate on a target workpiece.

Control electronics (not shown) monitor the implantation dose reaching the implantation station 506 and increase or decrease the ion beam concentration based upon a desired doping level for the silicon wafers 526 at the implantation station 506. This may include, for example utilizing a Faraday cup 524 that intersects the ion beam to monitor beam dose. The implantation station 506 includes a moveable wafer support 532 for the wafers 526. During loading of the moveable support 532, wafers are withdrawn from a wafer cassette 528 by a robotic arm 530 and inserted through a load-lock (not shown) into an implantation chamber 534. The moveable support 532 is rotated by a motor 540 about a center axis 542 to cause wafers placed on an outer periphery of the moveable support 526 to pass through the ion beam 504.

The ion beam source assembly 502 includes a source housing 544 about which a source magnet is located. In the example illustrated, the source magnet includes multiple source magnet components 546a, 546b that may, for example, correspond to a yoke 544a and coil 544b of an electromagnet. A set of ground electrodes 550 and an additional set of electrodes 552 are included to help confine the beam 504 before entering the analyzing magnet 520. Similarly, another set of electrodes 554, a set of plates 556 defining a resolving aperture and a subsequent set of electrodes 558 can be included to block spurious ions and maintain the confined beam 504.

Beam current can be modulated to achieve desired ion implantation by selectively controlling one or more components downstream of the ion source assembly 502, as well as one or more components more closely associated with the ion source assembly 502. For example, voltages applied to the extraction suppression electrodes 510, ground electrodes 550, electrodes 552, electrodes 554, plates 556 and electrodes 558 can be selectively regulated to modulate beam current. Similarly, the source magnet 546 and the neutralizing plasma source 516 can also be selectively adjusted to modulate the beam current.

The ion implantation system 500 further includes a monitoring system having a detector assembly 570 to detect particles, features, and other such detectable quantities on one or more wafers 526, for example, before, during, or after ion implantation. The monitoring system 570 may be mounted rotationally opposite, for example, or at another angular position from the ion beam path 504 on the moveable wafer support 532 within ion chamber 534. The monitoring system 570 includes a light source 572, for example, a laser light source 572 directed by an optical fiber 573 toward the one or more wafers 526 or other such workpieces mounted on the spinning wafer support 532.

In accordance with the present invention, the detector assembly 570 also includes one or more detectors 574 to receive scattered light from a spot on the wafers 526 illuminated by the laser light 572. The wafers 526 mounted on the wafer support 532 rotates and traverses under the beam of laser light 572 during ion implantation to detect the scattered light from the full surface of the wafers 526. In another aspect of the invention, the detected light may then be mapped with respect to the X-Y motion encoder positions corresponding to each wafer for image display and/or particle or other such feature analysis. In another aspect of the invention, the detected light may then be mapped with respect to X-Y motion encoder positions corresponding to each wafer (e.g., using a processor or computer) for image display and/or particle or other such feature analysis. Although positional encoders are employed in one example, defect positions may alternatively be determined in other ways, for example, through use of an optical position detector.

Although the implantation systems of FIGS. 3–5 are directed to batch type systems, it should be understood that the present invention may also be employed in conjunction with a single wafer type system employing either a one-dimensional or two-dimensional workpiece transport system. For example, in a so-called pencil-beam type system, the workpiece can be translated so that the beam will be scanned two-dimensionally across the wafer to effectively paint the entire workpiece for implantation thereof. Alternatively, a so-called ribbon beam system may be employed, wherein either beam or workpiece are scanned or translated one-dimensionally with respect to one another to create a similar painting effect.

In addition, while one aspect of the present invention provides for a single light source, a plurality of light sources may alternatively be employed in which each of the light sources illuminate a predetermined segment or portion of the workpiece. In another alternative arrangement, one or more light sources are employed and are directed at portions of the workpiece (either a test or production workpiece), wherein any particle count information ascertained therefrom is utilized to approximate a particle count for the entire wafer. Lastly, although position information associated with detected particles is provided in one aspect of the invention, the invention may be employed in instances where particle count information is collected without any positional data associated therewith being collected, and such alternatives are contemplated as falling within the scope of the present invention.

Figures 6A, 6B:
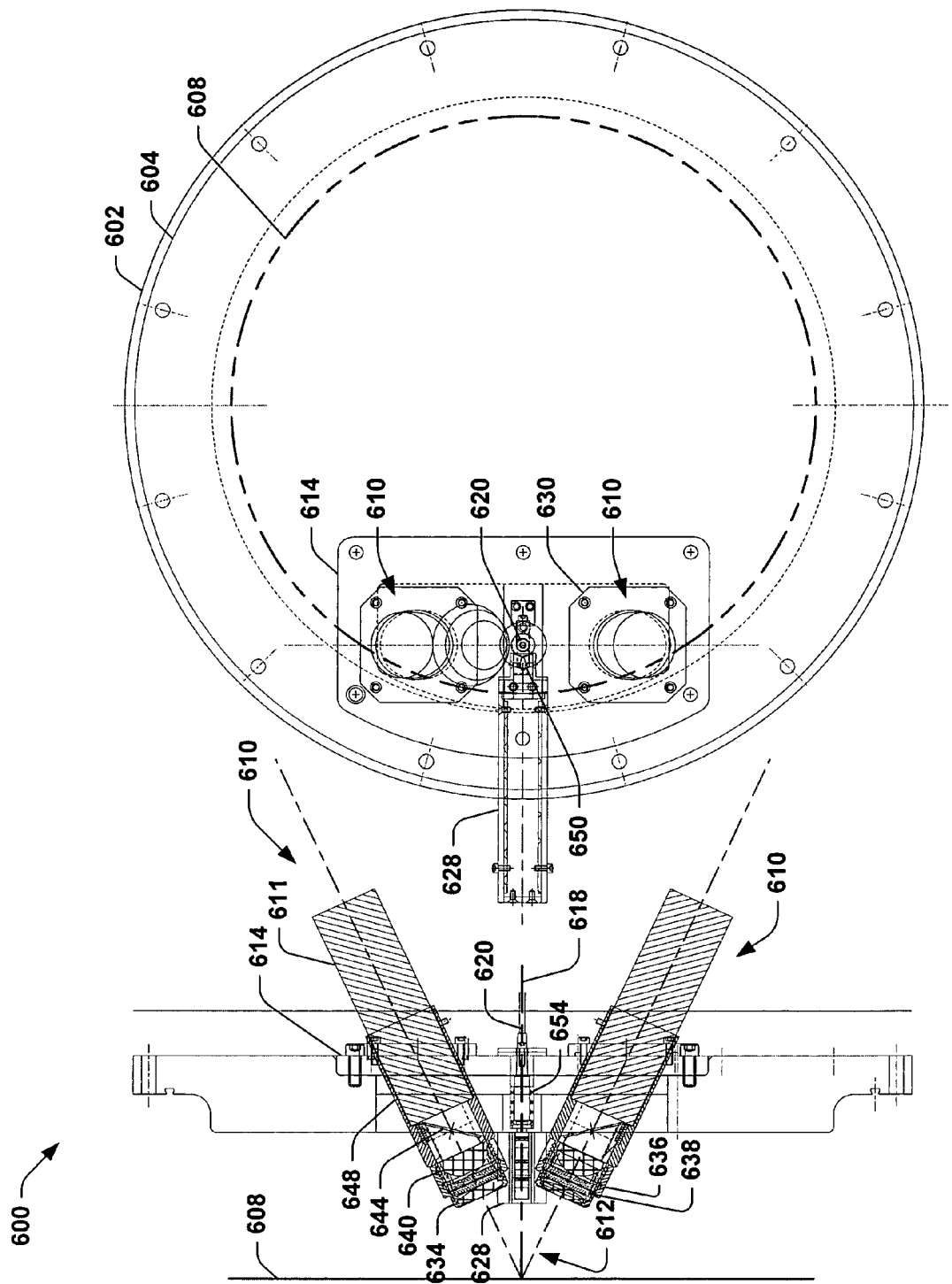
FIGS. 6A, 6B and 6C is a cross sectional side view, a front view, and a cross sectional top view, respectively, illustrating an exemplary detector assembly of an in-situ monitoring system wherein one or more aspects of the present invention are implemented.
Figure 6C:
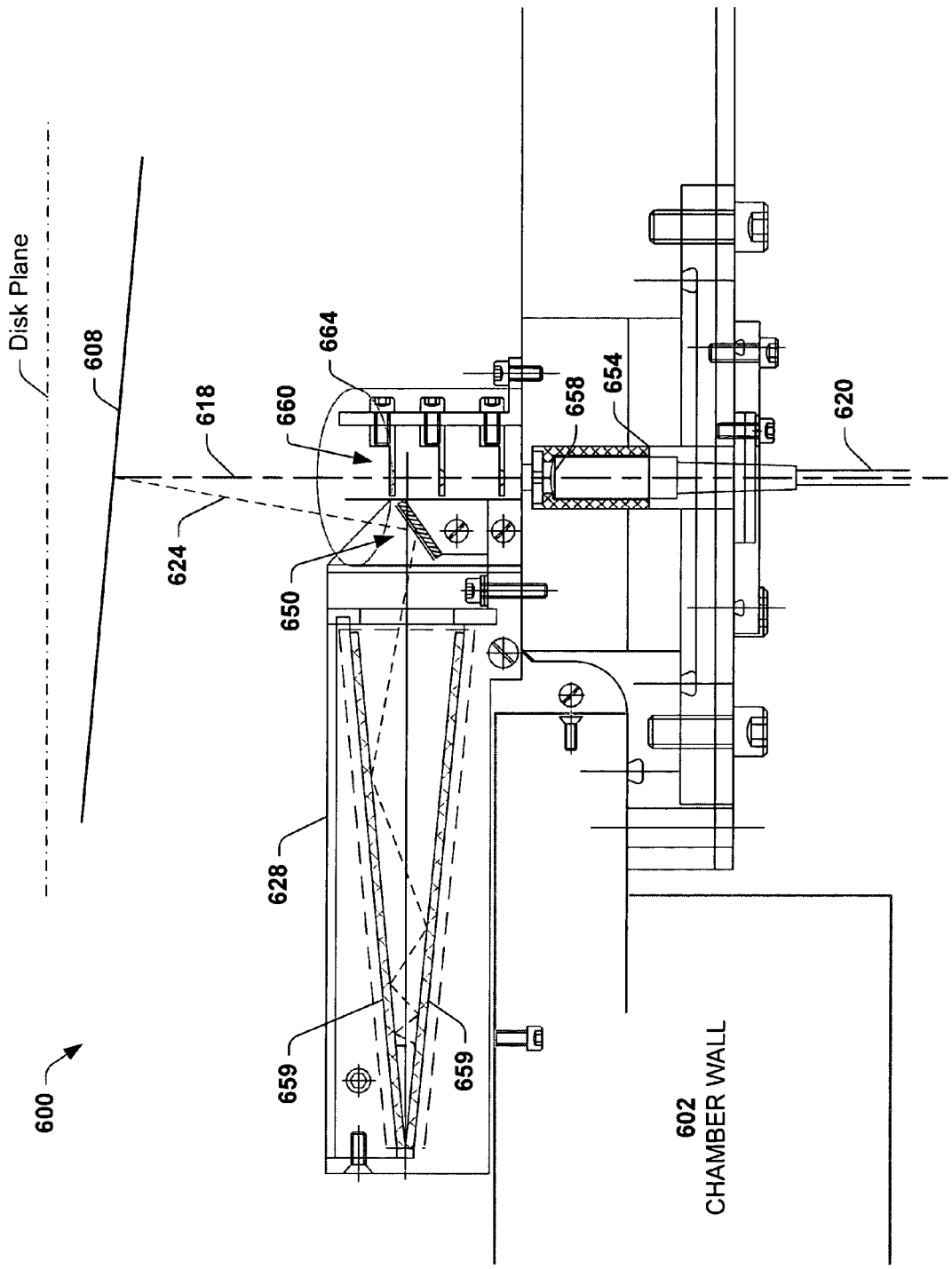

FIGS. 6A, 6B and 6C illustrate a cross sectional side view, a front view, and a cross sectional top view, respectively, of an exemplary detector assembly 600 of an in-situ monitoring system similar to those of FIGS. 1–5, wherein one or more aspects of the present invention are implemented.

FIGS. 7–12 further illustrate various views of the ion implantation and the in-situ monitoring system wherein the detector assembly 600 is shown in relationship to the wafers, the wafer support and the chamber within which the ion implantation and the in-situ monitoring take place. Detector assembly 600 of FIGS. 6A, 6B and 6C, for example, is mounted on an opening in the chamber wall 602 (e.g., chamber 534) on a plexiglass flange 604 over one of the wafers 608 mounted on a movable wafer support (e.g., 452, 532). The exemplary detector assembly 600 includes one or more (e.g., two) detectors 610 comprising, for example, a photomultiplier (PMT) 611 for detection of scattered light 612 from an illuminated spot on one of the wafers 608. Each detector 610 is affixed by a detector mount 614 at complimentary incident angles on either side of a laser beam 618 for illumination of the spot on the wafers 608. The laser beam 618 is directed by an optical fiber 620, for example, (or other means) toward the surface of the wafers 608 producing a spot on the wafers 608 scanned rotationally and linearly past the laser beam on the opposite side of the spinning wafer support 532 from an ion beam 504.

In operation, the two detectors 610 are used to maximize the signal and provide a second viewing angle for better detection resolution of the scattered light 612 and to provide detection off-axis from the impinging laser beam 618 or from the laser specular reflection 624. The specular reflection 624 is captured by a laser beam trap (or laser beam dump) 628 to prevent reflections inside the chamber 602 of the end station from blinding the detectors 610 with unwanted background light. The detectors 610 are held to the detector mount 614 by a PMT flange 630. As the particles or features detected may be much smaller than the laser beam 618, multiple scan passes of the wafers 608 in front of the laser beam 618 provide additional opportunities for scattered light detection at any particular instant for greater detection resolution. In addition, the processor (e.g., 330) may analyze the multiple passes of scattered light detections combining the resulting signals and looking for peaks in the detections corresponding to particles at a mapped location.

The two detectors 610 of the exemplary detector assembly 600 capture the scattered light 612 from the illuminated laser spot on the wafers 608. Scattered light 612 is collimated by a first lens 634 held by a lens housing 636, the light then passes thru a filter 638 to filter-out unwanted wavelengths, is focused by a second lens 640 and masked by slit 644 into the detector PMT 611 held by PMT housing 648. Slit 644 is used rather than an aperture, in one example, to admit light from both ends of the wafer linear scan. Advantageously, the slit masks specular reflections 624 yet admits the scattered light 612 for detection. In the above manner, the assembly can be thought of as having a detector with optional accompanying optics.

The exemplary detector assembly 600 further includes a fiber optic clamp 654 to hold a fiber optic head 658 of the optical fiber 620 substantially immobilized from motion of the optical fiber 620 and align the laser beam 618 to illuminate a predetermined spot on the wafers 608 (see FIG. 6C). The beam trap 628 of the detector assembly 600 further includes a mirror 650 to reflect the laser specular reflections 624 thru a window (shown later as 804) in the beam trap 628 to two neutral density filters 659 held at high angles of incidence to attenuate or absorb power from the laser specular reflections 624 with each interior reflection.

Three apertures 660, in this example, may also be used with the detector and may be enclosed in an aperture housing 664 as illustrated on the chamber side of the detector assembly 600 to define the shape of the laser beam to the wafers 608.

Figure 7:
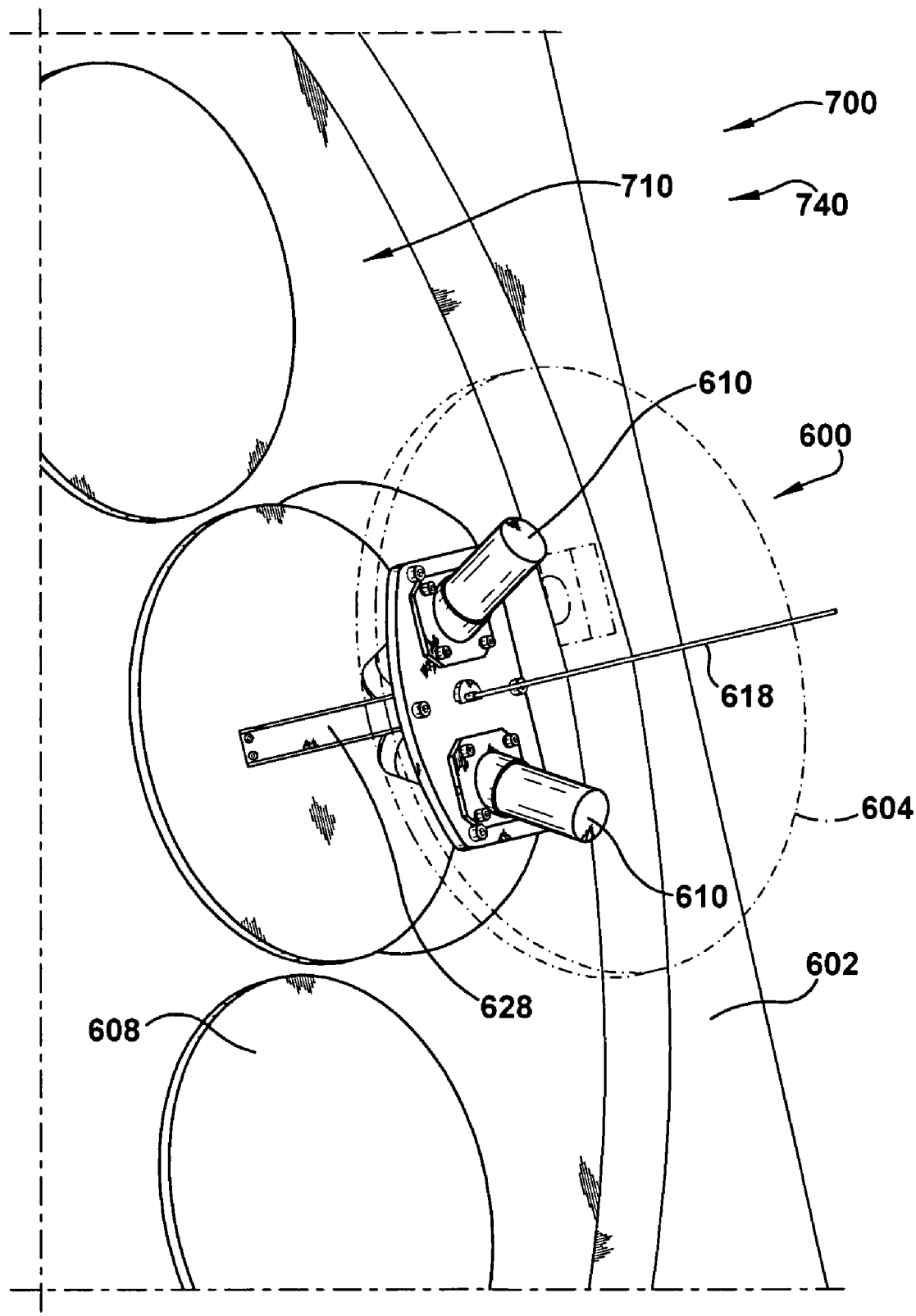
FIGS. 7 and 8 are perspective views of various components of an exemplary in-situ monitoring system end station portion used in a spinning disk batch ion implantation system similar to the system of FIGS. 4 and 5 to detect particles on one or more workpieces during ion implantation in accordance with one or more aspects of the present invention.
Figure 8:
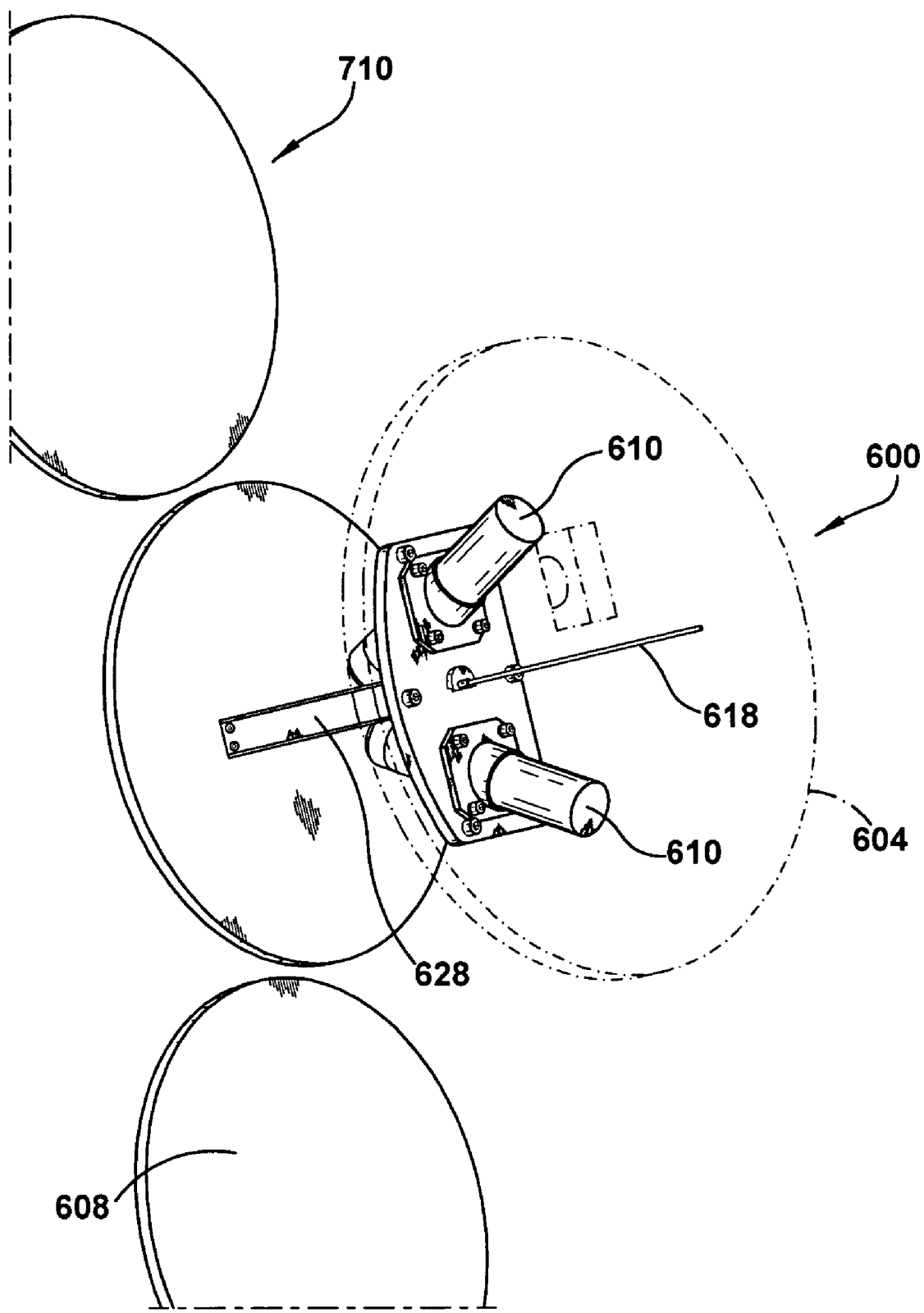

FIGS. 7 and 8 illustrate perspective views of various components of an exemplary in-situ monitoring system end station 700 used in a spinning disk batch ion implantation system similar to the system of FIGS. 4 and 5 of the present invention. The in-situ monitoring system end station 700 includes a detector assembly 600 similar to that of FIG. 6 to detect particles on one or more workpieces 608 during ion implantation in accordance with one or more aspects of the present invention. FIGS. 7 and 8 show an exemplary wafer assembly 710 comprising a movable wafer support holding up to 13 wafers 608 within an evacuated chamber 740 of an ion implantation end station (e.g., 310, 506). The detector assembly 600 is mounted opposite the ion beam as previously indicated, however, could also be located at another position if desired.

Figure 9:
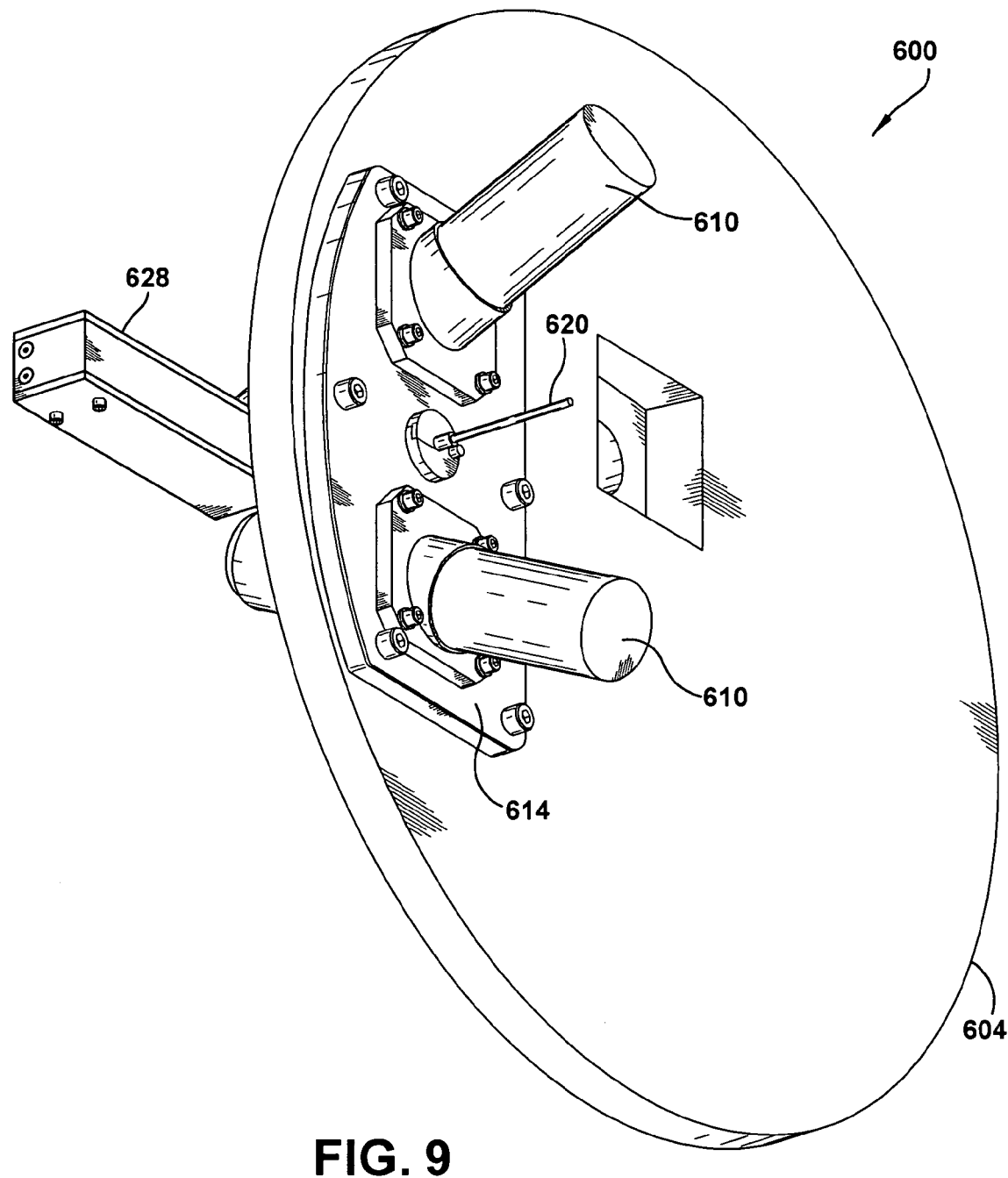
FIGS. 9 and 10 are perspective views illustrating a detector assembly for the in-situ monitoring system components of FIGS. 7 and 8 in accordance with one or more aspects of the present invention.
Figure 10:
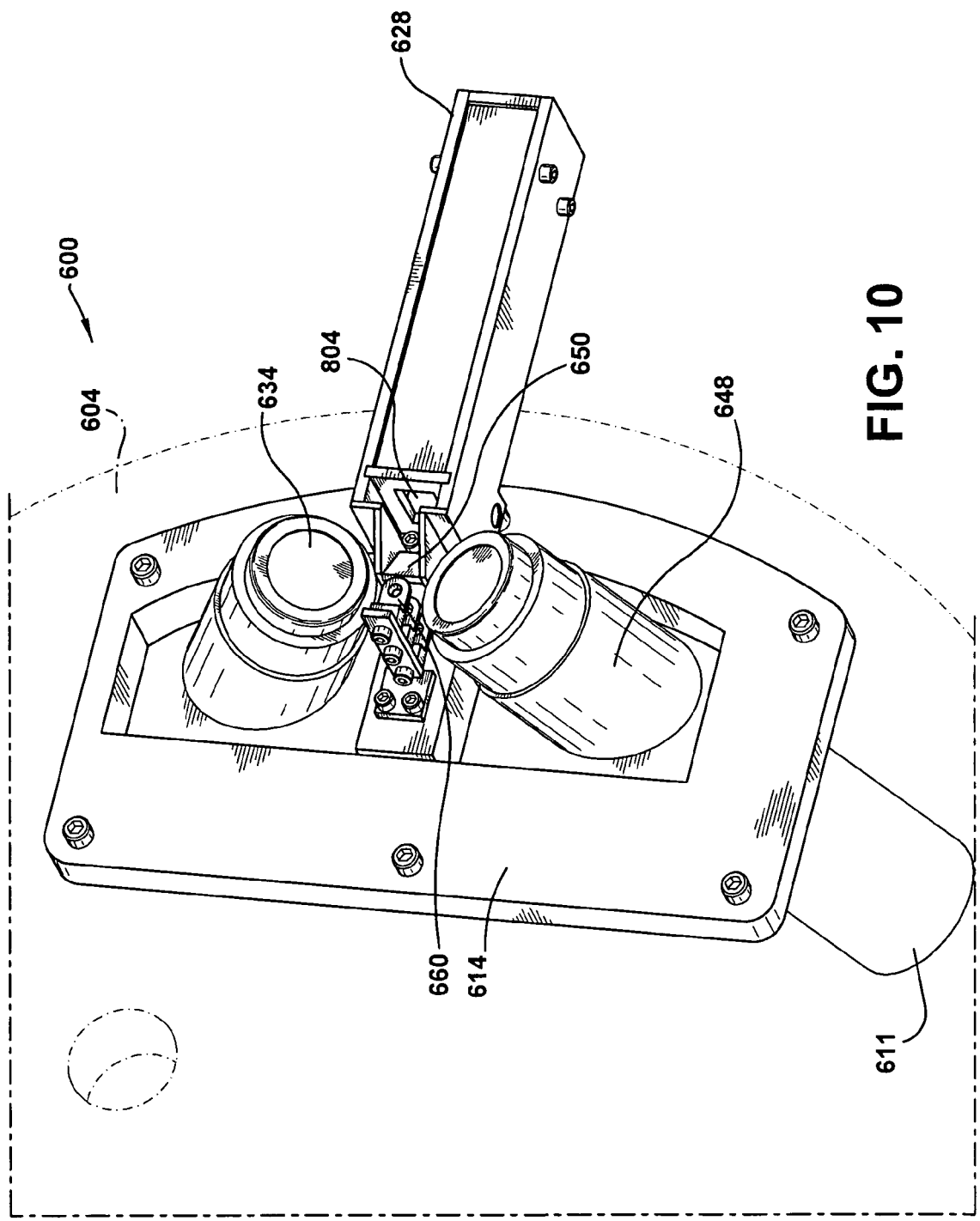

FIGS. 9 and 10 further illustrate perspective views of the detector assembly 600 for the in-situ monitoring system components of FIGS. 6–8 in accordance with one or more aspects of the present invention. FIGS. 9 and 10 better illustrate the orientation of the beam trap 628 with respect to the detectors 610, and that the beam trap is situated between the detectors to capture the laser specular reflections 624 reflected from the laser illuminated surface of the wafers 608. The specular light 624 enters the beam trap 628 by reflecting off the beam trap mirror 650 and entering thru a window 804 in the beam trap 628 between the two neutral density filters 659 which absorb the laser light energy. Also shown in FIG. 10, are the three apertures 660 that may be enclosed in an aperture housing 664 on the chamber side of the detector assembly 600 to define the shape of the laser beam to the wafers 608.

Figure 11:
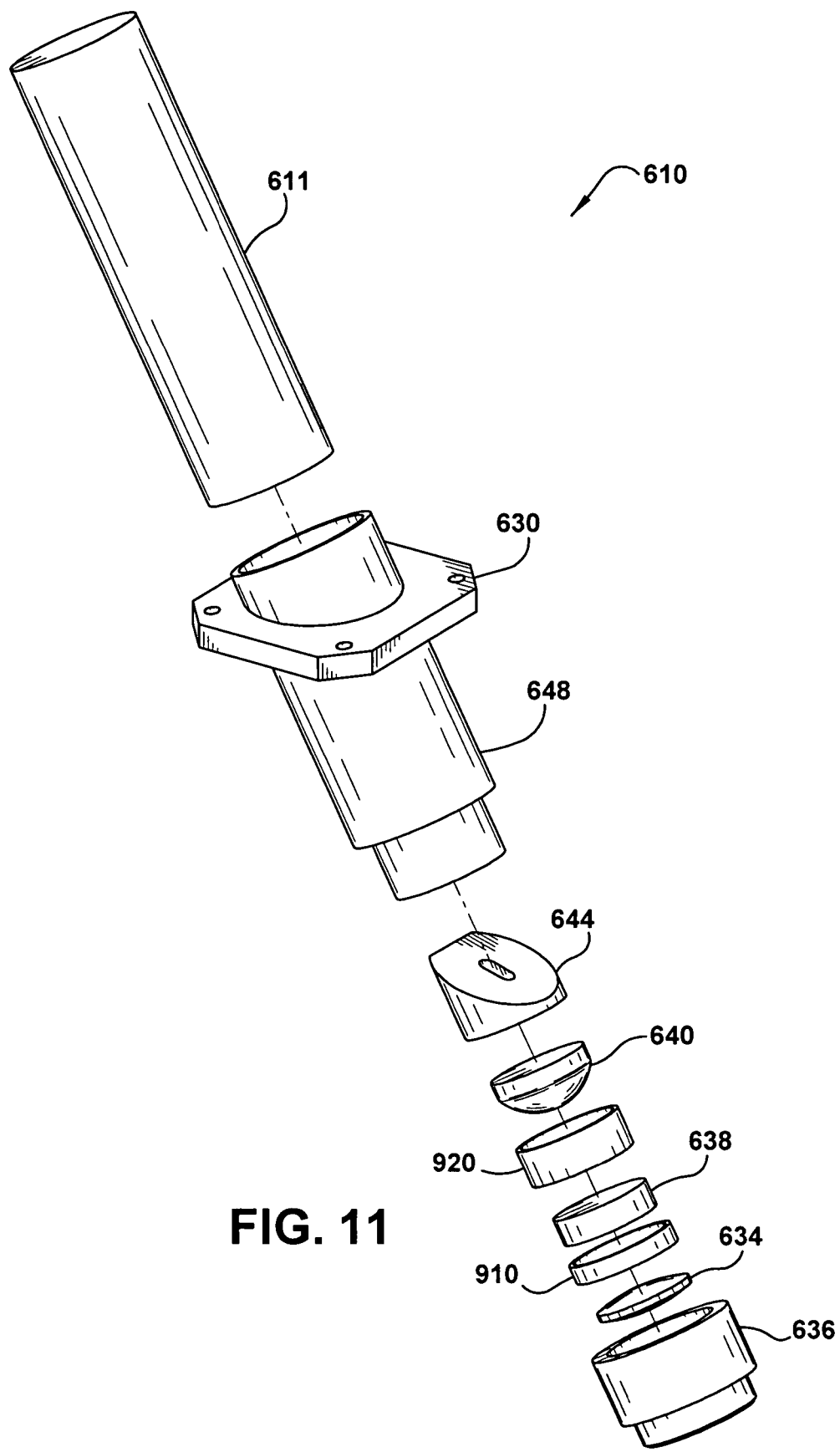
FIG. 11 is a perspective view illustrating an exemplary PMT detector and optics for the detector assembly of FIGS. 9 and 10 to detect scattered light in accordance with one or more aspects of the present invention.

Turning to FIG. 11, a perspective view illustrates an exemplary PMT detector 610 utilized in the detector assembly 600 of FIGS. 9 and 10 to detect scattered light 612 in accordance with one or more aspects of the present invention. The PMT detector 610 comprises a PMT 611, an optical stack to direct the scattered light 612 to the PMT detector 611 and mounting hardware to enclose the various components and seal the PMT from the vacuum in the chamber 740. Therefore the detector assembly 600 comprises a detector 610 with optional accompanying optics, as will be discussed in greater detail below.

As previously indicated, before detection by the PMT detector 610, the scattered light 612 is collimated by the first lens 634, which is held by a lens housing 636. The collimated light then passes thru a filter 638 to filter-out unwanted wavelengths, the filter 638 being held between a first spacer 910 and a second spacer 920. The collimated and filtered light is then focused by a second lens 640 and masked by slit 644 and passed into detector PMT 611 held by PMT housing 648. PMT flange 630 mechanically mounts the PMT 611 and lens assembly at a predetermined angle for best scattered light reception and seals the detector assembly 600 to the chamber 740. Slit 644 is used to admit light from both ends of the wafer linear scan as the distance to the wafer varies across the linear scan. Advantageously, the slit masks specular reflections 624 yet admits the scattered light 612 for detection to the PMT.

Figure 12:
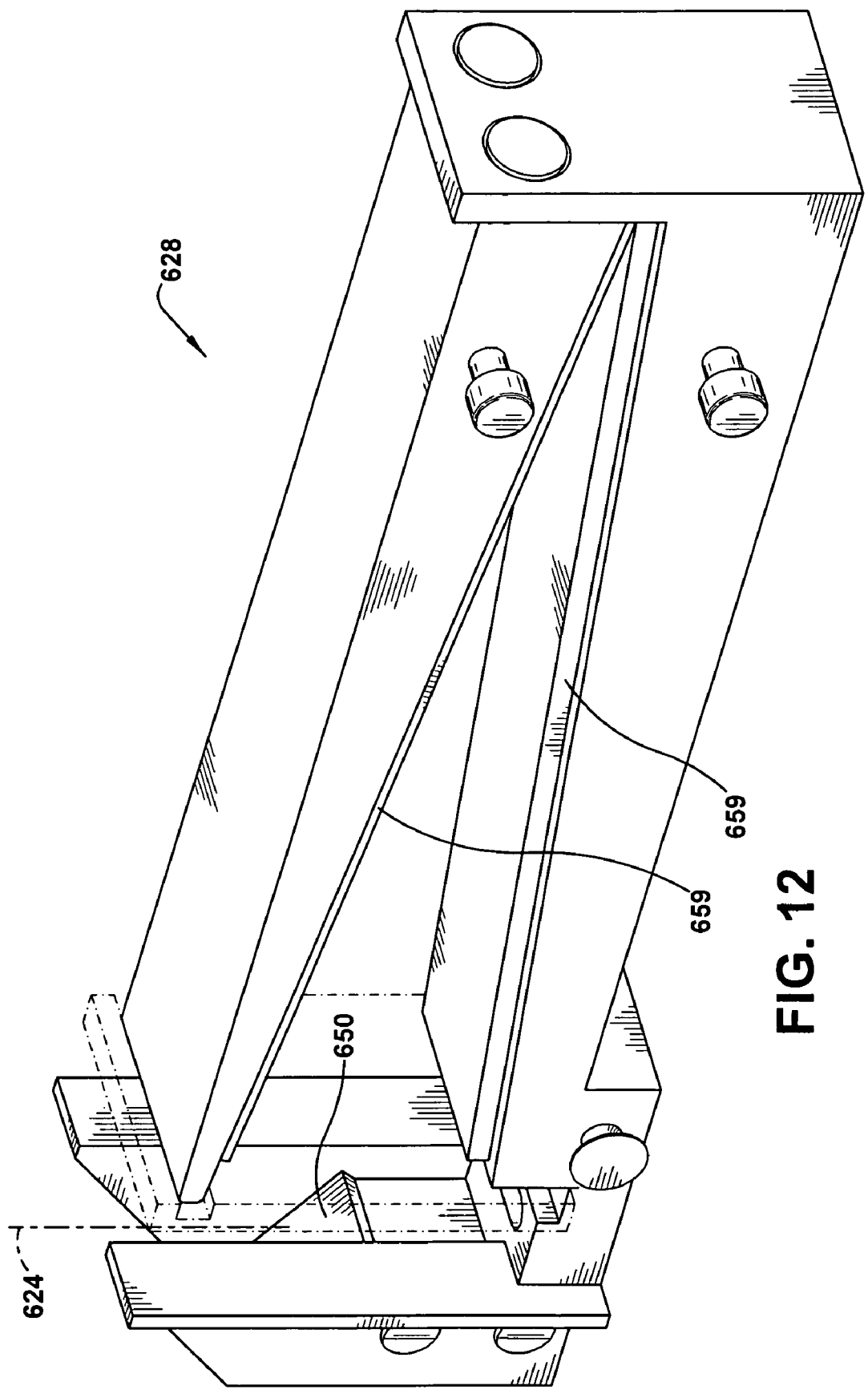
FIG. 12 is a perspective view of an exemplary laser beam dump for the detector assembly illustrated in FIGS. 7–10 to attenuate specular laser light in accordance with one or more aspects of the present invention.

FIG. 12 is perspective view of an exemplary laser beam dump or laser beam trap 628 for the detector assembly 600 illustrated in FIGS. 7–10 in accordance with one or more aspects of the present invention. As discussed, the laser beam dump or laser beam trap 628 attenuates specular laser light 624 reflected from the wafer, by bouncing the light reflected off mirror 650 back and forth between two neutral density filters 659 to increasingly absorb laser energy. The attenuated specular reflections 624 are thus inhibited from producing reflected light within the chamber of the end station and unwanted background signal within the detectors 610.

It will be appreciated that the present invention contemplates and has application to single and multiple wafer batch type spinning disk ion implantation systems and other such ion implantation systems. Additionally, it will also be appreciated that the monitoring systems illustrated herein may have application using a fixed laser beam or another such light source for scattered light detection and a movable workpiece having two or more axis of motion. Thus, in accordance with one or more aspects of the present invention, the particle detection, feature detection, or thermal detection systems illustrated herein may be accomplished before, during or after ion implantation.

Although the invention has been illustrated and described above with respect to a certain aspects and implementations, it will be appreciated that equivalent alterations and modifications will occur to others skilled in the art upon the reading and understanding of this specification and the annexed drawings. In particular regard to the various functions performed by the above described components (assemblies, devices, circuits, systems, etc.), the terms (including a reference to a "means") used to describe such components are intended to correspond, unless otherwise indicated, to any component which performs the specified function of the described component (i.e., that is functionally equivalent), even though not structurally equivalent to the disclosed structure, which performs the function in the herein illustrated exemplary implementations of the invention. In addition, while a particular feature of the invention may have been disclosed with respect to only one of several implementations, such feature may be combined with one or more other features of the other implementations as may be desired and advantageous for any given or particular application. Furthermore, to the extent that the terms "includes", "including", "has", "having", "with" and variants thereof are used, these terms are intended to be inclusive in a manner similar to the term "comprising". Also, the term "exemplary" as utilized herein simply means example, rather than finest performer.

What is claimed is:

1. An ion implantation system suitable for use in implanting ions into one or more workpieces and for detecting particles on the workpieces comprising:
   an ion implanter for producing a beam of ions and directing the beam of ions downstream toward the one or more workpieces held within an end station, the end station comprising:
      a rotary scan transport for providing rotary motion to the workpieces and an encoder count of the radial scan position; and
      a linear scan transport for providing reciprocating linear motion to the workpieces and an encoder count of the linear scan position; and
   an in-situ monitoring system associated with the end station suitable for detecting the particles on the one or more workpieces during ion implantation comprising:
      a light source for providing a fixed beam of illumination to a portion of one of the workpieces;
      two detectors symmetrically affixed on either side of the light source and both oriented toward the illuminated portion of the workpiece for capturing scattered light from opposite viewing angles of the illuminated portion of the workpiece; and
      a processor configured to analyze the intensity of the scattered light detected from the illuminated workpiece, and for mapping the light detected to a unique position on a workpiece determined by the encoder counts associated with the rotary and linear transports.

2. The system of claim 1 further comprising a display device coupled to the processor for displaying patterns of the scattered light mapped to the unique position on the workpiece.

3. The system of claim 1, wherein the processor is further operable to analyze the light mapped to the unique position on the workpiece and determine whether such position corresponds to a particle, scratch, feature, feature damage, or temperature of the workpieces.

4. The system of claim 3, wherein the processor is further operable to trigger a system alarm based on a comparison of the pattern determination to a threshold level of one of the detected particles, scratches, features, feature damage, and the temperature of the workpieces.

5. The system of claim 1, wherein the one or more workpieces comprise one or more semiconductor wafers.

6. The system of claim 1, wherein the light source comprises a laser.

7. The system of claim 6, wherein the laser light source is directed toward the workpiece using an optical fiber.

8. The system of claim 6, further comprising a laser beam trap having two neutral density filters to extinguish specular reflection of light from the laser.

9. The system of claim 1, wherein the processor comprises a computer.

10. The system of claim 1, wherein the detector comprises a photo-multiplier tube or a photodiode.

11. The system of claim 1, wherein the processor is further operable to analyze and compare the light received by the two detectors from the opposite viewing angles of the illuminated portion of the workpiece and to identify patterns associated with one of the detected particles, scratches, features, feature damage, and the temperature of the workpieces.

12. The system of claim 1, further comprising a laser beam trap having a mirror and two neutral density filters to extinguish specular reflection of light from the laser, the trap located between the two detectors.

13. The system of claim 1, further comprising a display device coupled to the processor for displaying patterns of the light mapped to the unique positions on the one or more workpieces.

14. The system of claim 1, wherein the ion implantation system comprises a batch implanter.

15. The system of claim 1, wherein the ion implantation system comprises a spinning disc batch implanter.

16. The system of claim 1, wherein the workpieces are held in the end station at a non-zero angle relative to a plane of the rotary motion to provide a wafer clamping force as the disk spins and a tilt implant angle of about 5 degrees, the detector further comprising a slit to pass the scattered light imaged to the detector and also to mask specular reflected light from the light source from saturating the detector.

17. The system of claim 1, wherein the detector further comprises:
   a first lens to collimate the scattered light;
   a filter to absorb unwanted wavelengths of the light;
   a second lens to focus the light; and
   a slit used to pass the scattered light to the detector and also to mask specular reflected light from saturating the detector.

18. The system of claim 17, wherein the scattered light passes from the first lens to the detector in an optical column, the order of the optical column comprising: the first lens, the filter, the second lens, the slit, and the detector.

19. The system of claim 1, wherein the in-situ monitoring system comprises two dissimilar detectors, wherein one detector monitors scattered light from the workpiece and the other detector monitors one of scattered light, infrared radiation, and a wavelength of the electromagnetic spectrum.

20. A system for detecting particles on one or more workpieces of an ion implantation system, the system comprising:
   an ion implanter for producing a beam of ions and directing the beam of ions downstream toward the one or more workpieces held within an end station, the end station comprising:
      a rotary scan transport for providing rotary motion to the workpieces and an encoder count of the radial scan position; and
      a linear scan transport for providing reciprocating linear motion to the workpieces and an encoder count of the linear scan position; and
   an in-situ monitoring system suitable for detecting particles and defects on the one or more workpieces during ion implantation, the system comprising:
      a laser light source conveyed by an optical fiber for providing a fixed beam of illumination to a portion of one of the workpieces;
      two detectors symmetrically affixed on either side of the light source and both oriented toward the illuminated portion of the workpiece for capturing scattered light from opposite viewing angles of the illuminated portion of the workpiece; and
      a processor adapted to analyze the intensity of the scattered light detected from the illuminated workpiece, and for mapping the light detected to a unique position on a workpiece determined by the encoder counts associated with the rotary and linear transports.

21. The system of claim 20 further comprising a display device coupled to the processor for displaying patterns of the scattered light mapped to the unique position on the workpiece.

22. The system of claim 20, wherein the processor is further operable to analyze the light mapped to the unique position on the workpiece and determine whether such position corresponds to a particle, scratch, feature, or feature damage.

23. The system of claim 22, wherein the processor is further operable to trigger a system alarm based on a comparison of the pattern determination to a threshold level of one of the detected particles, scratches, features, feature damage, and the temperature of the workpieces.

24. The system of claim 20, wherein the one or more workpieces comprise one or more semiconductor wafers.

25. The system of claim 22, wherein the processor is further operable to analyze and compare the light received by the two detectors from the opposite viewing angles of the illuminated portion of the workpiece and to identify patterns associated with one of the detected particles, scratches, features, feature damage, and the temperature of the workpieces.

26. The system of claim 20, further comprising a laser beam trap having two neutral density filters to extinguish specular reflection of light from the laser.

27. The system of claim 20, wherein the processor comprises a computer.

28. The system of claim 20, wherein the detector comprises a photo-multiplier tube or a photodiode.

29. The system of claim 20, further comprising a laser beam trap having a mirror and two neutral density filters to extinguish specular reflection of light from the laser, the trap located between the two detectors.

30. The system of claim 20, further comprising a display device coupled to the processor for displaying patterns of the light mapped to the unique positions on the one or more workpieces.

31. The system of claim 20, wherein the ion implanter comprises a batch implanter.

32. The system of claim 20, wherein the ion implanter comprises a spinning disc batch implanter.

33. The system of claim 20, wherein the workpieces are held in the end station at a non-zero angle relative to a plane of the rotary motion to provide a wafer clamping force as the disk spins and a tilt implant angle of about 5 degrees, the detector further comprising a slit to pass the scattered light imaged to the detector and also to mask specular reflected light from the light source from saturating the detector.

34. The system of claim 20, wherein the detector further comprises:
   a first lens to collimate the scattered light;
   a filter to absorb unwanted wavelengths of the light;
   a second lens to focus the light; and
   a slit used to pass the scattered light to the detector and also to mask specular reflected light from saturating the detector.

35. The system of claim 20, wherein the scattered light passes from the first lens to the detector in an optical column, the order of the optical column comprising: the first lens, the filter, the second lens, the slit, and the detector.

36. The system of claim 20, wherein the rotational and linear motion transports comprise one or more motion drives used to provide a compound motion for the detection scanning and ion implantation scanning of the wafers.

37. The system of claim 20, wherein the rotational and linear motion transports comprise separate drive motions for the detection scanning and ion implantation scanning operations.

38. The system of claim 20, wherein the in-situ monitoring system comprises two dissimilar detectors, wherein one detector monitors scattered light from the workpiece and the other detector monitors one of scattered light, infrared radiation, and a wavelength of the electromagnetic spectrum.

39. A method of particle detection on one or more workpieces within a spinning disk ion implantation system during ion implantation having an in-situ monitoring system comprising two detectors symmetrically affixed on either side of a light source, the detectors oriented toward the illuminated portion of one of the workpieces, the method comprising:
   spinning the workpieces;
   implanting ions into the workpieces by directing an ion beam toward the workpieces on the spinning disk;
   illuminating the one or more workpieces by directing a light beam from the light source toward the workpieces; and
   detecting scattered light received by the two detectors from each side of the illuminated portion of the one or more workpieces during ion implantation.

40. The method of claim 39, further comprising analyzing the detected scattered light corresponding to a position of the spinning disk to determine patterns of light corresponding to particles, analyzing and comparing the light received by the two detectors from opposite viewing angles of the illuminated portion of the workpiece, and identifying patterns associated with one of the detected particles, scratches, features, feature damage, and the temperature of the workpieces.

41. The method of claim 40, wherein the number of particles detected on one or more workpieces are counted.

42. The method of claim 41, wherein the particles count number is compared to a threshold level of particles to disable the ion implantation operations.

43. The method of claim 39, further comprising displaying the detected scattered light.

44. The method of claim 39, wherein the detection takes place before ion implantation operations.

45. The method of claim 39, wherein the detection takes place after ion implantation operations.

46. The method of claim 39, further comprising detecting a magnitude of the scattered light and estimating a size of a detected particles based on the detected magnitude.

47. The method of claim 46, further comprising binning a plurality of detected particles into one of a plurality of bins associated with estimated detected particle ranges.

48. The method of claim 47, further comprising investigating one or more particle contamination sources based on the binning of the detected particles.

49. An ion implantation system suitable for use in implanting ions into one or more workpieces and for detecting particles on the one or more workpieces, comprising:
   an ion implanter configured to provide a scan transport to the one or more workpieces with respect to an ion beam; and an in-situ monitoring system suitable for detecting particles on the one or more workpieces, comprising:
a laser light source conveyed by an optical fiber and configured to provide a beam of illumination to a portion of the one or more workpieces; and
two detectors symmetrically affixed on either side of the light source and oriented toward the illuminated portion of the workpiece and configured to capture scattered light from opposite viewing angles of the illuminated portion of the one or more workpieces.

50. The ion implantation system of claim 49, further comprising a processor configured to analyze the intensity of the scattered light detected from the illuminated portion of the one or more workpieces.

51. The ion implantation system of claim 50, wherein the processor is further configured to map the light detected to a unique position associated with the one or more workpieces.

52. The ion implantation system of claim 51, further comprising an encoder configured to provide an encoder count indicative of a scan position.

53. The ion implantation system of claim 49, wherein the transport comprises a linear scan transport for providing a reciprocating linear motion to the one or more workpieces with respect to the ion beam.

54. The ion implantation system of claim 53, wherein the transport further comprises a rotary scan transport configured to provide rotary motion to the one or more workpieces with respect to the ion beam.

* * * * *